United States Patent [19]

Lang

[11] Patent Number: 4,692,536

[45] Date of Patent: Sep. 8, 1987

[54] PROCESS FOR THE PREPARATION OF HEMIAMINALS, HEMIAMINALS AND THE USE THEREOF

[75] Inventor: Robert W. Lang, Pratteln, Switzerland

[73] Assignee: Ciba-Geigy Corporation, Ardsley, N.Y.

[21] Appl. No.: 917,948

[22] Filed: Oct. 14, 1986

[30] Foreign Application Priority Data

Oct. 21, 1985 [CH] Switzerland ............... 4515/85

[51] Int. Cl.$^4$ .............. C07F 7/10; C07F 7/18
[52] U.S. Cl. .................. 556/413; 556/415; 556/419; 556/420; 556/423; 556/424
[58] Field of Search ........... 556/413, 415, 420, 419, 556/423, 424

[56] References Cited

U.S. PATENT DOCUMENTS

| | | | |
|---|---|---|---|
| 2,541,154 | 2/1951 | Clapsadle | 556/413 X |
| 2,852,569 | 9/1956 | Braid | 260/633 |
| 2,852,569 | 9/1956 | Braid | 260/633 |
| 2,870,213 | 1/1959 | Woolf | 260/601 |
| 2,870,213 | 1/1959 | Woolf | 260/601 |
| 2,885,419 | 5/1959 | Beinfest et al. | 556/413 |
| 2,902,389 | 9/1959 | Keil | 556/413 X |
| 3,038,941 | 6/1962 | Stallmann | 260/603 |
| 3,038,941 | 6/1962 | Stallmann | 260/603 |
| 3,290,333 | 12/1966 | Fainberg et al. | 260/340.6 |
| 3,344,193 | 9/1967 | Carr et al. | 260/601 |
| 3,344,193 | 9/1967 | Corr et al. | 260/601 |
| 4,434,289 | 2/1984 | Findeisen et al. | 556/413 X |
| 4,636,568 | 1/1987 | Simon et al. | 556/413 X |

FOREIGN PATENT DOCUMENTS

| | | |
|---|---|---|
| 113467 | 7/1984 | European Pat. Off. |
| 155885 | 9/1985 | European Pat. Off. |
| 1091549 | 11/1967 | United Kingdom |
| 1414323 | 11/1975 | United Kingdom |
| 1484117 | 8/1977 | United Kingdom |
| 155885 | 9/1985 | European Pat. Off. |
| 1091549 | 11/1967 | United Kingdom |
| 1414323 | 11/1975 | United Kingdom |
| 1484117 | 8/1977 | United Kingdom |

OTHER PUBLICATIONS

Tetrahedron Letters; No. 35, pp. 3867–3870 (1968).
Houben-Weyl, "Methoden der Organischen Chemie", Band E3 (1983), pp. 383–386.
Tetrahedron Letters, vol. 24, No. 11, pp. 1143–1146 (1983).
Houben-Weyl, vol. E3, Aldehyde, pp. 685–687 (1983).
Houben-Weyl, "Methoden der Organischen Chemie", Band E3 (1983), pp. 383–386.
Pure and Applied Chem., vol. 48, pp. 275–285 (1976).

Primary Examiner—Paul F. Shaver
Attorney, Agent, or Firm—Irving M. Fishman; Michael W. Glynn

[57] ABSTRACT

The reaction of dimethylformamide, $R^1R^2R^3SiX$ and RY in the presence of zinc or the reaction of dimethylformamide, $R^1R^2R^3SiX$ and a zinc compound $RZnY \cdot yL$ affords hemiaminals of formula I

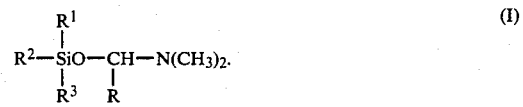

R is e.g. polyhalogenated alkyl containing at least one fluorine atom; $R^1$, $R^2$ and $R^3$ are e.g. alkyl; L is a ligand; X is chlorine or bromine; Y is chlorine, bromine or iodine and y is 1 or 2.

13 Claims, No Drawings

PROCESS FOR THE PREPARATION OF HEMIAMINALS, HEMIAMINALS AND THE USE THEREOF

The present invention relates to a process for the preparation of hemiaminals by reaction of dimethylformamide, a monohalosilane and an organic polyhalide in the presence of zinc, in which process the organic polyhalide and zinc may also be employed in the form of an organic zinc halide complex. The invention further relates to the novel hemiaminals and to the use of said hemiaminals for the preparation of polyhalogenated aldehydes.

1,1,1-Trichloro-2-dimethylamino-2-trimethylsilyloxyethane is known from Tetrahedron Letters, pp. 3867-3870 (1968). The formylation of organometallic compounds based on lithium and magnesium using dimethylformamide is described e.g. in Tetrahedron Letters, p. 1143 (1983). The reaction of polyhalogenated organometallic compounds with dimethylformamide in the presence of a monohalosilane to give silylated hemiaminals is not known.

The present invention relates to a process for the preparation of hemiaminals of formula I

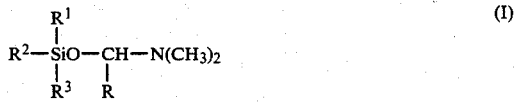

wherein R is unsubstituted or substituted polyhalogenated alkyl, cycloalkyl or aralkyl containing at least one fluorine atom and $R^1$, $R^2$ and $R^3$ are each independently a hydrogen atom, alkyl, cycloalkyl or aryl, which process comprises (a) reacting with one another at least equimolar amounts of dimethylformamide, a silane of formula II

wherein X is chlorine or bromine and $R^1$, $R^2$ and $R^3$ are as defined above, and a compound of formula III

wherein R is as defined above and Y is chlorine, bromine or iodine, in the presence of zinc, or (b) reacting with one another at least equimolar amounts of dimethylformamide, a silane of formula II and a zinc compound of formula IV

wherein R and Y are as defined above, L is a ligand and y is 1 or 2.

In the compounds of formulae I and II, $R^1$, $R^2$ and $R^3$ as alkyl are preferably linear or branched $C_1$–$C_{18}$alkyl, in particular $C_1$–$C_{12}$alkyl, most preferably $C_1$–$C_8$alkyl, as cycloalkyl they are preferably cyclopentyl or cyclohexyl and as aryl they are preferably phenyl. It is particularly preferred for $R^1$, $R^2$ and $R^3$ to be identical or different alkyl radicals, with $C_1$–$C_8$alkyl radicals being most preferred.

Examples of $R^1$, $R^2$ and $R^3$ are: methyl, ethyl, n-propyl, isopropyl, n-butyl, isobutyl, tert-butyl, pent-1-yl, 1-, 2- or 3-hexyl, 1,2,2-trimethyleth-1-yl, 1,1,2,2-tetramethyleth-1-yl (thexyl), heptyl, octyl, decyl, dodecyl, octadecyl, cyclohexyl, methylcyclohexyl, phenyl and methylphenyl.

Examples of the $R^1R^2R^3Si$ group are: silyl, methylsilyl, dimethylsilyl, trimethylsilyl, ethylsilyl, methylethylsilyl, diethylsilyl, triethylsilyl, dimethylethylsilyl, propylsilyl, isopropylsilyl, isopropyldimethylsilyl, tri-n-propylsilyl, tri-n-butylsilyl, n-butyldimethylsilyl, n-butyldiethylsilyl, tert-butyldimethylsilyl, tri-n-pentylsilyl, n-pentyldimethylsilyl, (1,2,2-trimethyleth-1-yl)dimethylsilyl, (1,1,2,2-tetramethylethyl)dimethylsilyl, tri-n-octylsilyl and n-octyldimethylsilyl.

The radical R in formulae I, III and IV is polyhalogenated with fluorine. Said fluorine may be partially substituted by chlorine and/or bromine. The radical R may be substituted or unsubstituted. If R is substituted, then it preferably contains 1 to 3 substituents, in particular 1 or 2 substituents, most preferably 1 substituent.

Suitable substituents are e.g. selected from the group consisting of —$NO_2$, —CN, —COR', —COOR', —CON(R')$_2$, $C_1$–$C_{12}$alkyl, $C_1$–$C_{12}$alkoxy, $C_1$–$C_{12}$alkylthio, $C_1$–$C_{12}$sulfoxyl, $C_1$–$C_{12}$sulfonyl, phenyl, benzyl, $C_3$–$C_{18}$trialkylsilyl, $C_3$–$C_{18}$trialkylsilyloxy, $C_1$–$C_{18}$alkylamino and di($C_1$–$C_{18}$)alkylamino, R' being a hydrogen atom, $C_1$–$C_{18}$alkyl, $C_4$–$C_8$cycloalkyl, phenyl or benzyl. R' as alkyl may be linear or branched and preferably contains 1 to 12 carbon atoms. Examples of further suitable substituents are heterocyclic radicals such as furyl, tetrafluoropyridyl, pyridyl or piperazyl. R' may also be such a heterocyclic radical. If R contains an aromatic group as substituent, then said group may be substituted by —OH or NR$_2$', —$NO_2$, —CN, —COR', —COOR', —CON(R')$_2$, $C_1$–$C_{12}$alkoxy, $C_1$–$C_{12}$alkylthio, $C_1$–$C_{12}$sulfoxyl or $C_1$–$C_{12}$sulfonyl.

In addition to —$NO_2$ and —CN, examples of substituents are also carbomethyl, carboethyl, carbophenyl, carboxy, carbomethoxy, carboethoxy, carbopropoxy, carbobutoxy, carbamino, methylcarbamino, dimethylcarbamino, ethylcarbamino, methylethylcarbamino, methyl, ethyl, n-propyl, isopropyl, n-butyl, isobutyl, tert-butyl, methoxy, ethoxy, propoxy, methylthio, trimethylsilyl, trimethylsilyloxy, methylamino, dimethylamino, methylethylamino.

R as polyhalogenated alkyl may be linear or branched and preferably contains 1 to 18, most preferably 1 to 12, carbon atoms. R as fluorinated cycloalkyl preferably contains 3 to 8 carbon atoms in the ring. R as fluorinated aralkyl is preferably α-fluoro-α-chlorobenzyl, α,α-difluorobenzyl, mono-, di-, tri-, tetra- or pentafluorophenylmethyl, mono-, di-, tri, tetra- or pentafluorophenylfluoromethyl or mono-, di-, tri-, tetra- or pentafluorophenyldifluoromethyl. R is preferably polyhalogenated with fluorine, chlorine and bromine, most preferably with fluorine and chlorine.

Examples of R are: $CF_3$, $CF_2Cl$, $CFCl_2$, $CF_2CF_3$, $CF_2ClCF_2$, $CCl_3CF_2$, $CF_3CCl_2$, $CF_3CFCl$, $CFCl_2CF_2$, $CFCl_2CCl_2$, $C_3F_9$, $CF_3CF_2CCl_2$, $C_nF_{2n+1}$ (perfluoroalkyl radicals) wherein n is 4 to 18, preferably 4 to 12, $C_6F_5CF_2$, $C_2H_5OOCCF_2$, $C_6H_5COCF_2$.

The compounds of formula II are either known or they can be prepared by known methods. Compounds of formula II wherein one of the radicals $R^1$, $R^2$ or $R^3$ contains a disubstituted α-carbon atom (e.g. the thexyl group) can be prepared by reacting monohalodialkylsilanes with tetrasubstituted ethylenes in the presence of $AlBr_3$ or $AlCl_3$. X in formula II is preferably chlorine.

The compounds of formula III are either known or they can be prepared by known methods. If Y is chlorine, then it is convenient to add catalytic amounts of iodine in order to accelerate the reaction.

The zinc compounds of formula IV are either known (q.v. U.S. Pat. No. 3,290,333) or they can be prepared by analogous methods. Furthermore, the zinc compounds of formula IV can also be obtained by displacing a more weakly attached ligand, e.g. ether, by an acid amide, e.g. dimethylformamide. If the zinc compounds of formula IV to be used are unstable, then it is convenient to employ them in solution and, if appropriate, not to prepare them until just before the reaction is carried out. In such cases it is preferable to use as solvents those corresponding to the ligand L.

L in formula II is preferably an aprotic solvent containing hetero atoms such as nitrogen, sulfur and oxygen. In particular, L is selected from the group consisting of ethers, carboxylates, lactones, sulfoxides, sulfones, N-substituted acid amides, and lactams.

Examples of suitable solvents are: ethers such as diethyl ether, dibutyl ether, tetrahydrofuran, dioxane, dimethylethylene glycol, dimethyldiethylene glycol, diethyldiethylene glycol, dibutyldiethylene glycol, dimethyltriethylene glycol, carboxylates and lactones such as propylene carbonate, ethyl acetate, methyl propionate, ethyl benzoate, ethyl glycol acetate, 2-methoxyethyl acetate, γ-butyrolactone, γ-valerolactone and mevalolactone, sulfoxides such as dimethyl sulfoxide and tetramethylene sulfoxide, sulfones such as dimethylsulfone, diethylsulfone, trimethylenesulfone and tetramethylenesulfone, and, in particular, acid amides such as dimethylformamide, dimethylacetamide, N-methylpyrrolidone and hexamethylphosphoric triamide.

The zinc is preferably activated in accordance with Fieser and Fieser, Reagents for Organic Synthesis, Vol. I, John Wiley, New York, p. 1276 (1976).

The process of the present invention can be carried out under the influence of ultrasound.

Reaction (a) is preferably carried out in the temperature range from −30° to 140° C., preferably from 0° to 80° C. Reaction (b) is preferably carried out in the temperature range from 20° to 200° C., preferably from 50° to 150° C.

The reactants are employed in at least equimolar amounts. However, the halosilane of formula II may also be employed in slight excess. In reaction (a), dimethylformamide can be used in a considerably higher amount and thereby act at the same time as solvent. An equimolar amount of dimethylformamide may also be employed, in which case it is recommended to use an inert solvent concomitantly. Suitable inert solvents are polar aprotic solvents such as those described above. In principle, the order in which the reactants are added is optional. However, since the reaction is exothermic, care must merely be taken that the final reactant is added slowly in order to prevent too great an increase in the reaction temperature. In a preferred embodiment, either zinc or the compound of formula III is introduced last into the mixture of the remaining reactants.

In reaction (b), the zinc compound of formula IV may be dissolved in an inert solvent, whereupon first dimethylformamide and then the halosilane of formula II, or vice-versa, are added to the resultant solution. It is advantageous to produce the zinc compound of formula IV directly before the reaction by reacting zinc with a compound of formula III in the presence of a solvent corresponding to the ligand L. In a preferred embodiment, L in formula IV is dimethylformamide and y is 2, and reaction (b) is advantageously carried out in the presence of an inert solvent, preferably dimethylformamide.

The process of this invention is advantageously carried out in an inert gas atmosphere (argon or nitrogen) and with the exclusion of moisture.

The hemiaminals of formula I are isolated in conventional manner. The reaction mixture can be extracted e.g. with a solvent such as a hydrocarbon (pentane, hexane, cyclohexane, petroleum ether). The extract is then washed and dried, after which the solvent is distilled off.

The process of the present invention makes polyhalogenated hemiaminals containing at least one fluorine atom generally accessible for the first time. The present invention further relates to hemiaminals of formula I

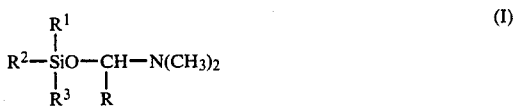

wherein R is unsubstituted or substituted polyhalogenated alkyl, cycloalkyl or aralkyl containing at least one fluorine atom and $R^1$, $R^2$ and $R^3$ are each independently a hydrogen atom, alkyl, cycloalkyl or aryl. For R, $R^1$, $R^2$ and $R^3$ the preferences described above apply.

The hemiaminals of formula I are valuable intermediates for the preparation of halogen-containing pharmaceutical and agrochemical substances. They are stable forms of polyhalogenated aldehydes. The invention also relates to the novel polyhalogenated aldehydes of the formula R-CHO (V), wherein R is as described above, with the preferences indicated above applying.

Aldehydes of the formula R-CHO can be prepared e.g. by hydrolysis of the hemiaminals with strong acids such as $H_2SO_4$, q.v. Houben-Weyl, Vol. E3: Aldehyde (Aldehydes), p. 685 ff. (1983).

A further object of the invention is the use of hemiaminals of formula I for the preparation of aldehydes of the formula R-CHO by hydrolysis with mineral acids.

The polyhalogenated aldehydes are valuable monomers for the cationic polymerisation for the preparation of PTFE-like polymers, q.v. Pure & Appl. Chem. 48, p. 276 (1976).

The invention is illustrated in more detail by the following Examples. Either nitrogen or argon is used as inert gas.

EXAMPLE 1

1,1,1-Trifluoro-2-dimethylamino-2-trimethylsilyloxyethane

In a 100 ml three-necked round flask, 3.3 g (50 mmol) of zinc dust (activated in accordance with Fieser & Fieser) and 6.0 g (55 mmol) of trimethylchlorosilane are added, in an inert gas atmosphere, to 50 ml of dimethylformamide, and the batch is cooled to 0° C. With vigorous stirring, 7.3 g (40 mmol) of trifluoroiodomethane are introduced over a glass frit in such a manner that the reaction temperature of the strongly exothermic reaction does not exceed 10° C. After stirring for 2 hours at room temperature, the yellow reaction solution is extracted with pentane, and the pentane phase is washed with $H_2O$, dried over $Na_2SO_4$ and subsequently concentrated by rotary evaporation at room temperature, affording the desired hemiaminal in 56% yield (4.8 g) and in high purity as a yellow oil.

$^1$H—NMR (250 MHz, CDCl$_3$): 0.16 ppm, s, 9H, 3 CH$_3$—Si; 2.36 ppm, s, 6H, 2 CH$_3$—N; 4.46 ppm, qa, JHF=5.5 Hz, 1H—C(2).

EXAMPLE 2

1,1,1,2,2-Pentafluoro-3-dimethylamino-3-thexyldimethylsilyloxypropane

In a 100 ml three-necked round flask, 3.3 g (50 mmol) of zinc dust and 9.8 g (55 mmol) of thexyldimethylchlorosilane are added, in an inert gas atmosphere, to 50 ml of dimethylformamide, and the batch is cooled to 0° C. With vigorous stirring, 13.5 g (55 mmol) of pentafluoroethyl iodide are introduced over a glass frit in such a manner that the reaction temperature of the exothermic reaction does not exceed 10° C. After stirring for 2 hours at room temperature, working up is effected as in Example 1, and the crude product is distilled under a high vacuum, affording the desired hemiaminal as a colourless oil in a yield of 62%.

b.p. 50° C./0.013 mbar, $^1$H—NMR (300 MHz, CDCl$_3$): 2.40 ppm, s, 6H, 2 CH$_3$—N; 4.54 ppm, d×d, JFH=10.0 Hz, 1H—C(3).

EXAMPLE 3

1,1-Dichloro-1-fluoro-2-dimethylamino-2-thexyldimethylsilyloxyethane

In a 100 ml bomb tube, 3.3 g (50 mmol) of zinc dust and 9.8 g (55 mmol) of thexyldimethylchlorosilane are added, in an inert gas atmosphere, to 50 ml of dimethylformamide. Then 7.6 g (55 mmol) of trichlorofluoromethane and a catalytic amount of iodine are added at 0° C. After 12 hours at 70° C., working up is effected as in Example 1, and the crude product is distilled under a high vacuum, affording the desired hemiaminal as a colourless oil in 43% yield (6.8 g).

b.p. 80° C./0.013 mbar: $^1$H—NMR (60 MHz, CDCl$_3$): 2.44 ppm, 2s, Δδ=2 Hz, 6H, 2 CH$_3$—N; 4.40 ppm, d, JHF=6.5 Hz, 1H—C(2).

EXAMPLE 4

1,1,1-Trifluoro-2,2-dichloro-3-dimethylamino-3-trimethylsilyloxypropane

In a 2.5 l sulfurating flask, 65.5 g (1.0 mol) of zinc dust are added, in an inert gas atmosphere, to 1000 ml of dimethylformamide. With vigorous stirring, a mixture of 187.5 g (1.0 mol) of 1,1,1-trifluorotrichloroethane and 130.2 g (1.2 mol) of trimethylchlorosilane is added dropwise at 0°–10° C., the zinc slowly going into solution in an exothermic reaction. After stirring for 2 hours at room temperature, working up is effected as in Example 1, affording the desired hemiaminal in 62% yield (182.5 g) and in high purity as a yellow oil.

$^1$H—NMR (250 MHz, CDCl$_3$): 0.21 ppm, s, 9H, 3 CH$_3$—Si; 2.49 ppm, s, 6H, 2 CH$_3$—N; 4.71, s, 1H—C(3).

EXAMPLE 5

1,1,1-Trifluoro-2,2-dichloro-3-dimethylamino-3-tert-butyldimethylsilyloxypropane In a 100 ml three-necked round flask, 2.2 g (33 mmol) of zinc dust and 4.5 g (30 mmol) of tert-butyldimethylchlorosilane are added, in an inert gas atmosphere, to 50 ml of dimethylformamide. Then 5.6 g (30 mmol) of 1,1,1-trifluorotrichloroethane are added dropwise at 0°–10° C. After the exothermic reaction has subsided, the reaction mixture is left for 2 hours at room temperature. After working up as in Example 1, the desired hemiaminal is obtained as a yellow oil in 42% yield (4.3 g).

b.p. 120° C./26 mbar; $^1$H—NMR (250 MHz, CDCl$_3$): 2.51 ppm, s, 6H, 2 CH$_3$—N; 4.70 ppm, s, 1H—C(3).

EXAMPLE 6

1,1,1-Trifluoro-2,2-dichloro-3-dimethylamino-3-thexyldimethylsiloxypropane

Method A: In a 250 ml three-necked round flask, 6.8 g (0.104 mol) of zinc dust and 17.8 g (0.10 mol) of thexyldimethylchlorosilane are added, in an inert gas atmosphere, to 100 ml of dimethylformamide. Then 20.7 g (0.11 mol) of 1,1,1-trifluorotrichloroethane are added dropwise at 0°–10° C. After the exothermic reaction has subsided, the reaction mixture is left for 2 hours at room temperature. After working up as in Example 1, the desired hemiaminal is obtained as a yellow oil in 70% yield (25.6 g).

b.p. 70° C./0.013 mbar; $^1$H—NMR (250 MHz, CDCl$_3$): 2.53 ppm, s, 6H, 2 CH$_3$—N; 4.72 ppm, s, 1H—C(3).

Method B: In a 500 ml three-necked round flask, 300 ml of dimethylformamide are slowly added dropwise, in an inert gas atmosphere and with good cooling, to 57.2 g (0.175 mol) of 2,2,2-trifluorodichloroethylzinc chloride.(diethyl ether)$_2$. After the exothermic reaction has subsided, 34.2 g (1.191 mol) of thexyldimethylchlorosilane are added, and the reaction mixture is heated for 2 hours to 80° C. Working up is effected as in Example 1; yield: 67% (43.1 g).

EXAMPLE 7

1,1-Difluoro-1-ethoxycarbonyl-2-dimethylamino-2-thexyldimethylsilyloxyethane

In a 250 ml three-necked round flask, 4.32 g (66 mmol) of zinc dust and 13.4 g (75 mmol) of thexyldimethylchlorosilane are added, in an inert gas atmosphere, to 120 ml of dimethylformamide. Then 9.51 g (60 mmol) of chlorodifluoroacetic acid are added dropwise at room temperature, and the reaction mixture is subsequently heated for 4 hours to 80° C. After working up as in Example 1, the desired hemiaminal is obtained as a pale yellow oil in 84% yield (17.0 g).

b.p. 120° C./0.013 mbar; $^1$H—NMR (250 MHz, CDCl$_3$): 2.36 ppm, s, 6H, 2 CH$_3$—N; 4.59 ppm, d×d, JHF=13.5 Hz, 1 H—C(2).

EXAMPLE 8

1,1,1-Trifluoro-2-dimethylamino-2-thexyldimethylsilyloxyethane

Following the procedure of Example 2 but using trifluoromethyl iodide instead of pentafluoroethyl iodide affords the desired hemiaminal as a colourless oil in 74% yield.

b.p. 60° C./0.013 mbar; $^1$H—NMR (250 MHz, CDCl$_3$): 2.40 ppm, s, 6H, 2 CH$_3$—N; 4.46 ppm, qa, JHF=5.5 Hz, 1 H—C(2).

EXAMPLE 9

1,1,1,2,2,3,3,4,4,5,5,6,6,7,7-Pentadecafluoro-8-dimethylamino-8-thexyldimethylsilyloxyoctane Following the procedure of Example 2 but using n-1-iodoperfluoroheptane instead of pentafluoroethyl iodide affords the desired hemiaminal as a colourless oil in 43% yield.

b.p. 80° C./0.0165 mbar; $^1$H—NMR (300 MHz, CDCl$_3$): 2.41 ppm, s, 6H, 2 CH$_3$—N; 4.60 ppm, t, JHF=11.25 Hz, 1 H—C(8).

APPLICATION EXAMPLE

EXAMPLE 10

2,2-Dichloro-3,3,3-trifluoropropanal

An apparatus consisting of a 250 ml three-necked round flask with N$_2$ inlet, a drip funnel and 2 cooling traps (−78° C.) attached at the outlet side is charged with 49.0 g (0.5 mol) of concentrated H$_2$SO$_4$. After heating the H$_2$SO$_4$ to 90° C., 149.0 g (0.5 mol) of 1,1,1-trifluoro-2,2-dichloro-3-dimethylamino-3-trimethyl-silyloxypropane are slowly added dropwise, and the aldehyde transported in the N$_2$ stream is condensed. The aldehyde redistills at 52° C./994 mbar in 83% yield (75.0 g) as a colourless oil.

$^1$H—NMR (60 MHz, CDCl$_3$): 9.30 ppm, qa, JHF=2.5 Hz, CHO.

What is claimed is:

1. A process for the preparation of a hemiaminal of formula I

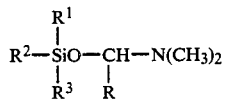
(I)

wherein R is unsubstituted or substituted polyhalogenated alkyl, cycloalkyl or aralkyl containing at least one fluorine atom and R$^1$, R$^2$ and R$^3$ are each independently a hydrogen atom, alkyl, cycloalkyl or aryl, which process comprises (a) reacting with one another at least equimolar amounts of dimethylformamide, a silane of formula II $$R^1R^2R^3SiX \quad (II)$$

wherein X is chlorine or bromine and R$^1$, R$^2$ and R$^3$ are as defined above, and a compound of formula III $$RY \quad (III)$$

wherein R is as defined above and Y is chlorine, bromine or iodine, in the presence of zinc, or (b) reacting with one another at least equimolar amounts of dimethylformamide, a silane of formula II and a zinc compound of formula IV $$RZnY.yL \quad (IV)$$

wherein R and Y are as defined above, L is a ligand and Y is 1 or 2.

2. A process according to claim 1, wherein reaction (a) is carried out in the temperature range from −30° C. to 140° C. and reaction (b) is carried out in the temperature range from 20° C. to 200° C.

3. A process according to claim 1, wherein X in formula II is chlorine.

4. A process according to claim 1, wherein in reaction (b) first the zinc compound of formula IV is produced by reacting a compound of formula III with zinc in the presence of a solvent corresponding to the ligand L.

5. A process according to claim 1, wherein L in formula IV is dimethylformamide and y is 2, and wherein reaction (b) is carried out in the presence of an inert solvent.

6. A process according to claim 1, wherein L in formula IV is an aprotic solvent containing hetero atoms.

7. A process according to claim 6, wherein L in formula IV is selected from the group consisting of ethers, carboxylates, lactones, sulfoxides, sulfones, N-substituted acid amides, and lactams.

8. A process according to claim 1, wherein the substituents for R in formula I are selected from the group consisting of —NO$_2$, —CN, —COR', —COOR', —CON(R')$_2$, C$_1$-C$_{12}$alkyl, C$_1$-C$_{12}$alkoxy, C$_1$-C$_{12}$alkylthio, C$_1$-C$_{12}$sulfoxyl, C$_1$-C$_{12}$sulfonyl, phenyl, benzyl, C$_3$-C$_{18}$trialkylsilyl, C$_3$-C$_{18}$trialkylsilyloxy, C$_1$-C$_{18}$alkylamino and di(C$_1$-C$_{18}$)alkylamino, R' being a hydrogen atom, C$_1$-C$_{18}$alkyl, C$_4$-C$_8$cycloalkyl, phenyl or benzyl.

9. A process according to claim 1, wherein R in formula I contains 1 to 3 substituents.

10. A process according to claim 1, wherein R$^1$, R$^2$ and R$^3$ are identical or different C$_1$-C$_8$alkyl radicals.

11. A process according to claim 1, wherein R in formula I is polyhalogenated with fluorine.

12. A process according to claim 1, wherein R in formula I is unsubstituted or substituted polyhalogenated C$_1$-C$_{18}$alkyl, polyhalogenated cycloalkyl containing 3 to 8 carbon atoms in the ring, or is polyhalogenated benzyl.

13. A hemiaminal of formula I

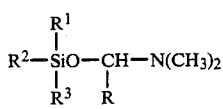
(I)

wherein R is unsubstituted or substituted polyhalogenated alkyl, cycloalkyl or aralkyl containing at least one fluorine atom and R$^1$, R$^2$ and R$^3$ are each independently a hydrogen atom, alkyl, cycloalkyl or aryl.

* * * * *